US010071231B2

(12) United States Patent
Yokota et al.

(10) Patent No.: US 10,071,231 B2
(45) Date of Patent: Sep. 11, 2018

(54) MEDICAL INSTRUMENT AND MEDICAL SYSTEM

(71) Applicant: OLYMPUS CORPORATION, Tokyo (JP)

(72) Inventors: Takuo Yokota, Tokyo (JP); Rei Matsunaga, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/587,591

(22) Filed: May 5, 2017

(65) Prior Publication Data
US 2017/0232237 A1 Aug. 17, 2017

Related U.S. Application Data

(63) Continuation of application No. PCT/JP2015/080222, filed on Oct. 27, 2015.

(30) Foreign Application Priority Data

Dec. 25, 2014 (JP) ................................. 2014-263066

(51) Int. Cl.
A61M 25/09 (2006.01)
A61B 17/04 (2006.01)

(52) U.S. Cl.
CPC ... A61M 25/09041 (2013.01); A61B 17/0483 (2013.01); A61B 17/0485 (2013.01)

(58) Field of Classification Search
CPC ............ A61B 17/0483; A61B 17/0485; A61B 2017/2212
See application file for complete search history.

(56) References Cited

U.S. PATENT DOCUMENTS 5,312,422 A * 5/1994 Trott .................. A61B 17/0469
604/272
5,499,991 A 3/1996 Garman et al.
(Continued)

FOREIGN PATENT DOCUMENTS

JP H09-327463 A 12/1997
JP 2008-011970 A 1/2008
JP 2008-289556 A 12/2008

OTHER PUBLICATIONS

International Search Report dated Jan. 26, 2016 issued in PCT/JP2015/080222.
(Continued)

Primary Examiner — Alexander Orkin
(74) Attorney, Agent, or Firm — Scully, Scott, Murphy & Presser, P.C.

(57) ABSTRACT

A medical instrument is that the first holding portion or the second holding portion is capable of moving so that a distance between a distal end of the first holding portion and a distal end of the second holding portion changes from a first dimension which is larger than a diameter of the wire to a second dimension which is smaller than the diameter of the wire and the space is formed by the first holding portion and the second holding portion such that the wire is capable of rotating about a line connecting a first contact point where the first protrusion portion contacts with the wire with a second contact point where the second protrusion portion contacts with the wire.

9 Claims, 18 Drawing Sheets

(56) References Cited

U.S. PATENT DOCUMENTS

| | | | |
|---|---|---|---|
| 5,653,716 A * | 8/1997 | Malo | A61B 17/0483 606/110 |
| 5,709,694 A * | 1/1998 | Greenberg | A61B 17/062 112/169 |
| 5,993,474 A | 11/1999 | Ouchi | |
| 6,132,439 A * | 10/2000 | Kontos | A61B 17/0469 606/139 |
| 7,651,503 B1 | 1/2010 | Coe et al. | |
| 2006/0069399 A1* | 3/2006 | Weisel | A61B 17/0483 606/148 |
| 2007/0038229 A1* | 2/2007 | de la Torre | A61B 17/0483 606/139 |
| 2007/0038230 A1* | 2/2007 | Stone | A61B 17/0482 606/139 |
| 2008/0009856 A1 | 1/2008 | Suzuki | |
| 2010/0241144 A1* | 9/2010 | Delli-Santi | A61B 17/00234 606/150 |
| 2011/0238078 A1 | 9/2011 | Goode et al. | |
| 2012/0209300 A1* | 8/2012 | Torrie | A61B 17/0469 606/148 |
| 2014/0336532 A1 | 11/2014 | Seguy | |

OTHER PUBLICATIONS

Japanese Office Action dated Sep. 21, 2016 received in Japanese Patent Application No. 2016-534260.
Extended Supplementary European Search Report dated Jul. 18, 2018 in European Patent Application No. 15 87 2469.0.

* cited by examiner

US 10,071,231 B2

MEDICAL INSTRUMENT AND MEDICAL SYSTEM

TECHNICAL FIELD

The present invention relates to a medical instrument and a medical system.

This application is a continuation application based on a PCT Patent Application No. PCT/JP2015/080222, filed on Oct. 27, 2015, whose priority is claimed on Japanese Patent Application No. 2014-263066, filed on Dec. 25, 2014, the entire contents of which are hereby incorporated by reference.

BACKGROUND ART

A method of introducing a medical instrument into a human hollow organ using a guide wire for treatment and examination of the human hollow organ is known. When obstruction such as stenosis or occlusion occurs at an opening of the hollow organ, the guide wire itself cannot be inserted into the hollow organ. For example, when a duodenal papilla is tightly closed, it is difficult to insert the guide wire into a desired hollow organ such as a bile duct or a pancreatic duct via the duodenal papilla.

As a solution in such a case, a method called a rendezvous method is known. In the rendezvous method, a guide wire introduced into a bile duct or a pancreatic duct from a site other than a duodenal papilla is caused to protrude from the duodenal papilla and an end of the protruding guide wire is held by a medical instrument. The guide wire protruding from the duodenal papilla into a duodenum is pulled to the outside of the body through a treatment instrument channel of an endoscope inserted into the duodenum. Then, a stent indwelling operation is performed by using the guide wire pulled to the outside of the body.

When indwelling a treatment instrument such as a stent by the rendezvous method, the treatment instrument is pushed into a bile duct or a pancreatic duct from a papilla through an endoscope channel similarly to a procedure of ordinary ERCP (Endoscopic Retrograde Cholangiopancreatography) or the like. However, there is a case where a duodenal papilla cannot be seen from a front side by an endoscopic image or the duodenal papilla may be closed tightly because of an anatomical structure of a patient. Further, there is a case where a running state of the bile duct imagined by a surgeon may be different from a real one. In such a case, even if the surgeon pushes the treatment instrument into the duodenal papilla by a manual operation since the treatment instrument in a space between a distal end of the endoscope and the papilla is bent and the pressing force is easily lost, it is difficult to introduce the treatment instrument into the duodenal papilla.

Therefore, a method of introducing a medical instrument holding a guide wire into the bile duct or the pancreatic duct by retracting the guide wire into the bile duct or the pancreatic duct instead of the above-described method of pulling the guide wire protruding into the duodenum from the duodenal papilla to the outside of the body through the treatment instrument channel has been proposed. A grasping forceps (for example, see Japanese Unexamined Patent Application, First Publication No. 2008-289556) is known as a medical instrument holding a guide wire.

SUMMARY OF INVENTION

A medical instrument which grips a wire according to a first aspect of the present invention includes: a sheath which has a longitudinal axis; a first holding portion which includes a first protrusion portion protruding inward in a radial direction of the sheath, and protrudes from a distal end of the sheath; and a second holding portion which includes a second protrusion portion facing the first protrusion portion, and protrudes from the distal end of the sheath. The first holding portion and the second holding portion are arranged with a gap therebetween so that a space in which the wire is held between the first protrusion portion and the second protrusion portion is formed. The first holding portion or the second holding portion is capable of moving so that a distance between a distal end of the first holding portion and a distal end of the second holding portion changes from a first dimension which is larger than a diameter of the wire to a second dimension which is smaller than the diameter of the wire and the space is formed by the first holding portion and the second holding portion such that the wire is capable of rotating about a line connecting a first contact point where the first protrusion portion contacts with the wire with a second contact point where the second protrusion portion contacts with the wire.

According to a medical instrument of a second aspect of the present invention, in the above-described first aspect, the first holding portion and the second holding portion may be arranged so that a protrusion direction of the first protrusion portion and a protrusion direction of the second protrusion portion directly face each other.

According to a medical instrument of a third aspect of the present invention, in the above-described first aspect, a gap between the first holding portion and the second holding portion distal end side of the may be larger at the distal end side of the first holding portion and the second holding portion than at the proximal end side of the first holding portion and the second holding portion.

According to a medical instrument of a fourth aspect of the present invention, in the above-described first aspect, the first protrusion portion may be arranged at a distal end portion of the first holding portion and the second protrusion portion may be arranged at a distal end portion of the first holding portion.

According to a medical instrument of a fifth aspect of the present invention, in the above-described first aspect, the first holding portion may be a hook member that is capable of holding the wire by hooking the wire, the second holding portion may be a protrusion portion which protrudes outward from the distal end of the sheath, the protrusion portion may be provided with a hole which is parallel to the longitudinal axis, and a distal end of the hook member may be capable of entering the hole.

According to a medical instrument of a sixth aspect of the present invention, in the above-described fifth aspect, a cross-sectional shape of a lumen of the sheath perpendicular to the longitudinal axis may include a long axis and a short axis and a cross-sectional shape of the hook member may include a long axis and a short axis.

According to a medical instrument of a seventh aspect of the present invention, in the above-described first aspect, an opening into which the wire is insertable may be formed by the distal end of the first holding portion and the distal end of the second holding portion. A dimension of the opening in the radial direction when the wire comes into point-contact with the first holding portion and the second holding portion may be smaller than the diameter of the wire.

According to a medical instrument of an eighth aspect of the present invention, in the above-described first aspect, the second holding portion may be arranged to be capable of advancing and retracting in a lumen of the sheath and the first holding portion and the second holding portion may be a two-legged forceps which is opened and closed by advancing and retracting relative to the sheath.

According to a medical instrument of a ninth aspect of the present invention, in the above-described first aspect, a lumen which is arranged along a lumen of the sheath and is different from the lumen may be further provided.

According to a medical instrument of a tenth aspect of the present invention, the medical instrument includes: a sheath which has a longitudinal axis; a first holding portion which is arranged to be capable of advancing and retracting in a lumen of the sheath and includes a first protrusion portion protruding inward in a radial direction of the sheath; and a second holding portion which includes a second protrusion portion and protrudes from the distal end of the sheath. The first holding portion and the second holding portion are arranged with a gap therebetween so that the first protrusion portion and the second protrusion portion face each other. When a wire is positioned between the first protrusion portion and the second protrusion portion and the first holding portion is retracted, the wire comes into point-contact with the first protrusion portion and the second protrusion portion.

A medical system of a tenth aspect of the present invention includes the wire and the medical instrument of any one of the above-described first to tenth aspects.

DESCRIPTION OF EMBODIMENTS

[First Embodiment]

A medical instrument according to a first embodiment of the present invention will be described with reference to FIGS. 1 to 16.

Figure 1:
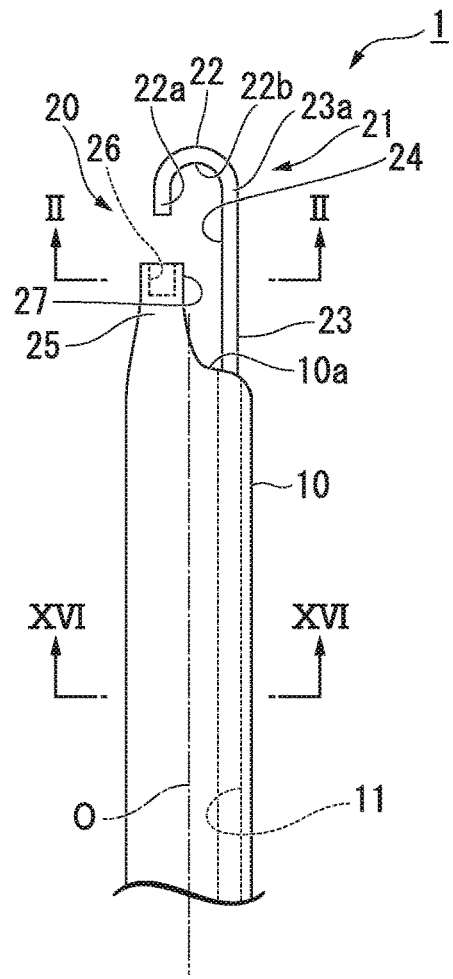
FIG. 1 is an overall view showing a medical instrument of a first embodiment of the present invention.

A medical instrument 1 of the present invention is a medical instrument which is capable of holding a wire, for example, a medical guide wire used while being inserted into the body. The medical instrument 1 includes, as shown in FIG. 1, a sheath 10 and a holding portion 20 including a first holding portion 21 and a second holding portion 25.

The sheath 10 has a center axis O and a lumen 11 of the sheath 10 is a columnar space.

The hook member (first holding portion) 21 is arranged to be capable of advancing and retracting in the lumen 11 of the sheath 10. The hook member 21 includes a hook portion 22 which is formed at a distal end side and a columnar bar-shaped portion 23 which extends toward a proximal end side. The hook portion 22 is configured to hold a guide wire W while being hooked thereto. The hook portion 22 and the bar-shaped portion 23 are integrally formed with each other. The hook portion 22 extends from a distal end 23a of the bar-shaped portion 23 toward a distal end side of the hook member 21 and a distal end 22a of the hook portion 22 is curved toward a proximal end of the hook portion 22. In the present embodiment, the hook portion 22 is curved by 180° and is formed in a substantially semicircular arc shape. Accordingly, a space which is opened below (toward a distal end 10a of the sheath 10) is formed by the distal end 22a and an inner peripheral surface 22b of the hook portion 22 and the distal end 23a of the bar-shaped portion 23.

Figure 2:
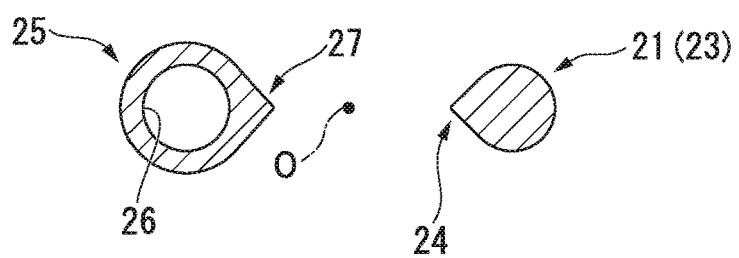
FIG. 2 is a cross-sectional view taken along a line II-II of the medical instrument of FIG. 1.

Further, the bar-shaped portion 23 includes a first protrusion portion 24 which protrudes inward in the radial direction of the sheath 10 as shown in FIG. 2 in a cross-section perpendicular to the longitudinal direction. The first protrusion portion 24 is provided to have a uniform range in the extension direction of the bar-shaped portion 23. The first protrusion portion 24 may be provided at a portion which protrudes from the distal end 10a of the sheath 10 in at least the bar-shaped portion 23 when the guide wire W is gripped (to be described later).

The protrusion portion (second holding portion) 25 protrudes outward from the distal end 10a of the sheath 10 (in the extension direction of the sheath 10) as shown in FIG. 1. The protrusion portion 25 is provided with a hole 26 which is parallel to the center axis O. Further, as shown in FIG. 2, the protrusion portion 25 includes a second protrusion portion 27 which protrudes inward in the radial direction of the sheath 10. The second protrusion portion 27 is provided throughout the longitudinal direction of the sheath 10.

Further, the hook member 21 and the protrusion portion 25 are arranged with a gap therebetween so that the protrusion direction of the first protrusion portion 24 and the protrusion direction of the second protrusion portion 27 directly face each other. In the present embodiment, as shown in the cross-section of FIG. 2, the hook member 21 and the protrusion portion 25 are arranged so that the protrusion direction of the first protrusion portion 24 and the protrusion direction of the second protrusion portion 27 face each other.

Figure 3:
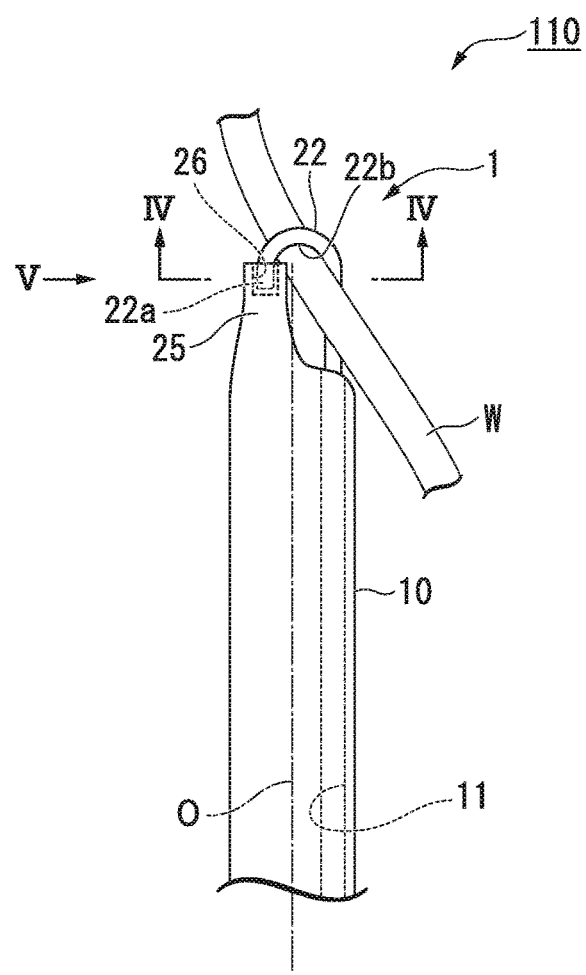
FIG. 3 is an overall view showing a state where the medical instrument of FIG. 1 holds a guide wire.
Figure 4:
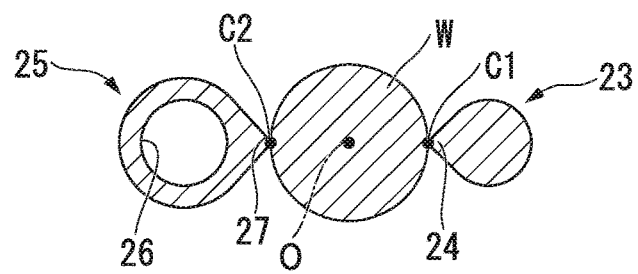
FIG. 4 is a cross-sectional view taken along a line IV-IV of the medical instrument of FIG. 3.

A medical system 110 of the present embodiment including the medical instrument 1 and the guide wire W having a circular cross-sectional shape will be described. As shown in FIG. 3, when the guide wire W is positioned between the first protrusion portion 24 and the second protrusion portion 27 and the hook member 21 is moved backward, the guide wire W comes into point-contact with the first protrusion portion 24 at a contact point C1 and the guide wire W comes into point-contact with the second protrusion portion 27 at a contact point C2 as shown in FIG. 4.

Figure 5:
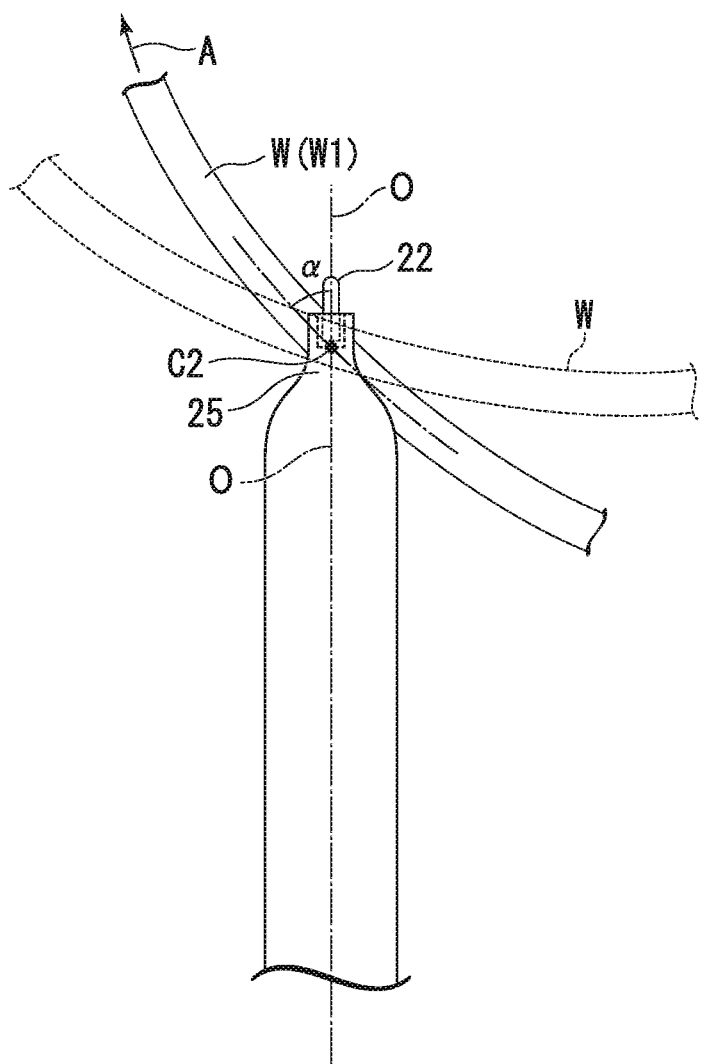
FIG. 5 is a diagram showing the medical instrument of FIG. 3 when viewed from a direction V.

That is, the guide wire W comes into point-contact with the holding portion 20 at two points which are the contact point C1 and the contact point C2. For this reason, when the guide wire W is pulled upward (in a direction indicated by an arrow A) as shown in FIG. 5, the guide wire W rotates about a line connecting the contact point C1 and the contact point C2 and serving as a rotation axis and the guide wire W and the center axis O form an acute angle therebetween at the side at which the guide wire W is pulled. That is, an angle α formed between the guide wire W and the center axis O becomes an acute angle.

Further, the hook member 21 may be formed, as shown in FIG. 3, so that a curvature radius of the inner peripheral surface 22b of the hook portion 22 becomes smaller than a curvature radius of the guide wire W. With such a configuration, since the guide wire does not contact the inner peripheral surface 22b even when the hook member 21 is retracted relative to the sheath 10, the guide wire W can rotate about the line connecting the contact point C1 and the contact point C2 and serving as the rotation axis.

Next, a method of introducing the medical instrument 1 into a hollow organ, for example, a bile duct by a rendezvous method will be described.

As the rendezvous method, there are two methods of puncturing a bile duct (first hollow organ) from the inside of the body and a method of puncturing the bile duct from the outside of the body. However, in the following description, an example of puncturing the bile duct Bd from the inside of the body is used. In addition, the cross-sectional shape of the guide wire W to be used is circular and the outer peripheral surface of the guide wire W has a curved surface.

[First Step]

Figure 6:
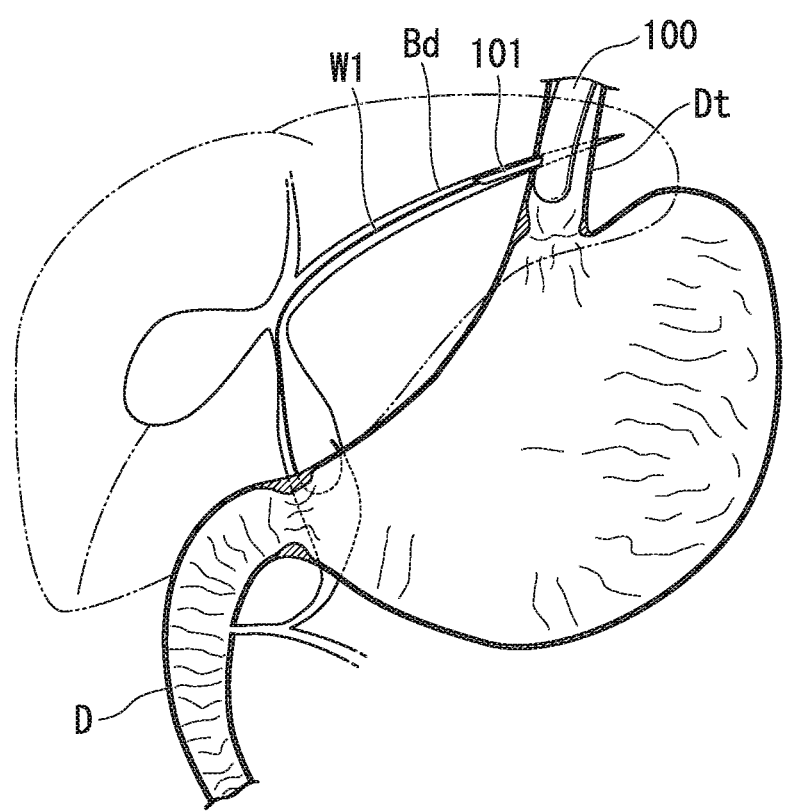
FIG. 6 is a diagram illustrating a method of introducing the medical instrument of the first embodiment of the present invention.

In the case of puncturing the bile duct from the inside of the body, a known ultrasonic endoscope is used. First, as shown in FIG. 6, an ultrasonic endoscope 100 is inserted orally into an alimentary canal Dt. Next, the bile duct Bd is confirmed with an ultrasonic image, a puncture needle 101 is inserted into the bile duct Bd through the alimentary canal Dt, and the guide wire W1 is caused to protrude from the puncture needle 101 to introduce the guide wire W1 into the bile duct Bd.

[Second Step]

Figure 7:
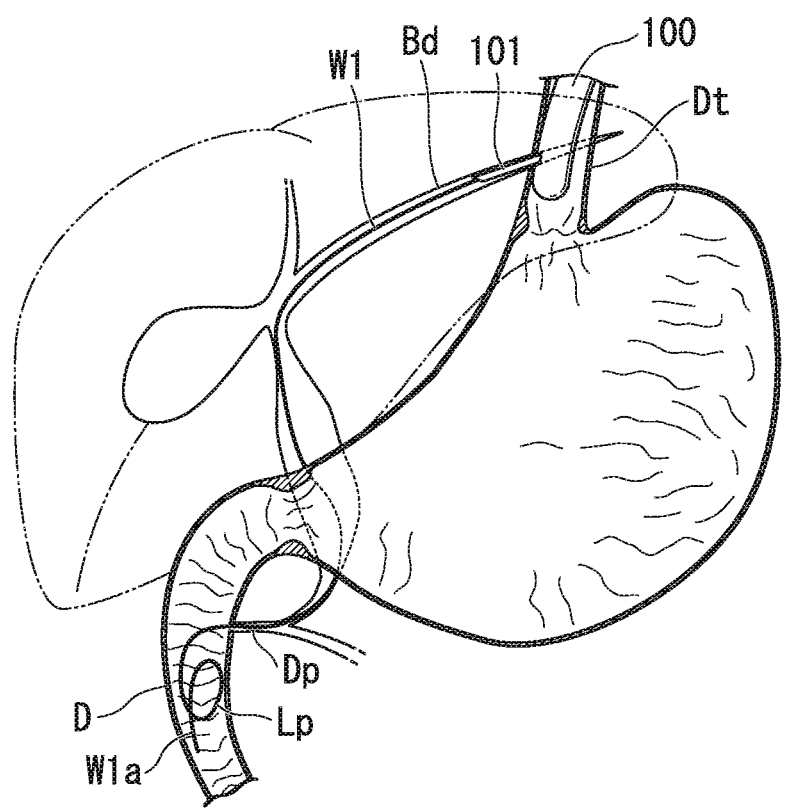
FIG. 7 is a diagram illustrating a method of introducing the medical instrument of the first embodiment of the present invention.

Next, as shown in FIG. 7, the surgeon presses the first guide wire W1 inserted into the bile duct Bd to cause a distal end W1a of the first guide wire W1 to protrude from a duodenal papilla (opening) Dp into a duodenum (second hollow organ) D. When the first guide wire W1 is pressed toward the duodenal papilla Dp, the distal end W1a of the first guide wire W1 protruding from the duodenal papilla Dp is introduced into the duodenum D so that a loop Lp is formed. Then, the ultrasonic endoscope 100 is removed to the outside of the body and the distal end W1a of the first guide wire W1 is indwelled in the duodenum D. At this time, the proximal end side of the first guide wire W1 is outside the patient's body.

By means of the loop Lp formed at the distal end of the first guide wire W1, it is possible to prevent the first guide wire W1 from coming out of the body together with the ultrasonic endoscope 100 when the ultrasonic endoscope 100 is removed to the outside of the body. In this manner, the distal end W1a of the first guide wire W1 is indwelled in the duodenum D.

[Third Step]

Figure 8:
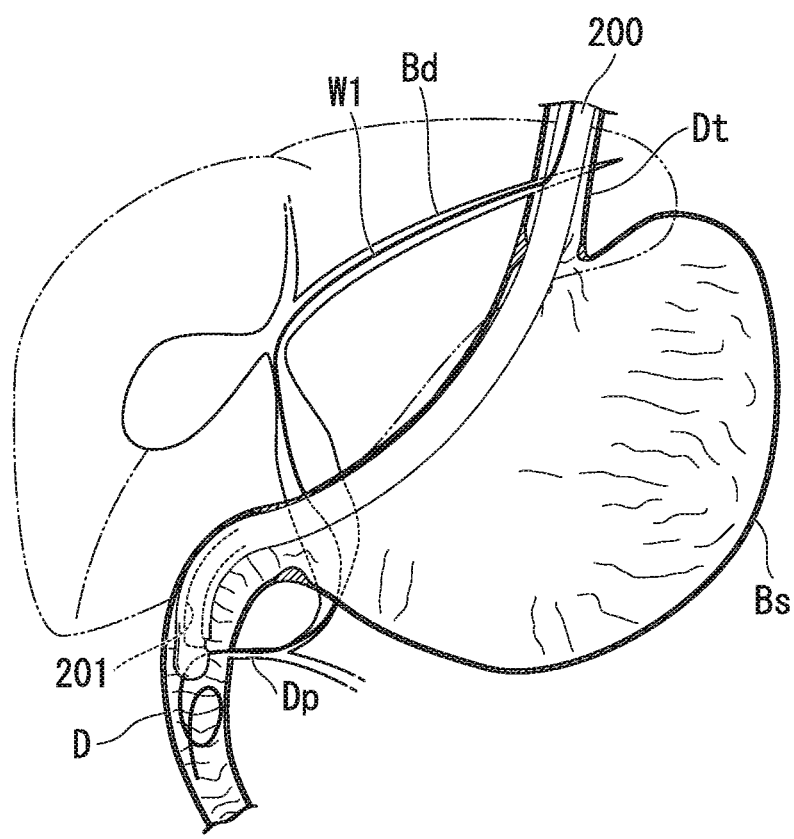
FIG. 8 is a diagram illustrating a method of introducing the medical instrument of the first embodiment of the present invention.

Next, as shown in FIG. 8, a side view type endoscope 200 is inserted to the vicinity of the duodenal papilla Dp via a stomach Bs. Then, the medical instrument 1 is inserted through a treatment instrument channel 201 of the endoscope 200.

[Fourth Step]

Figure 9:
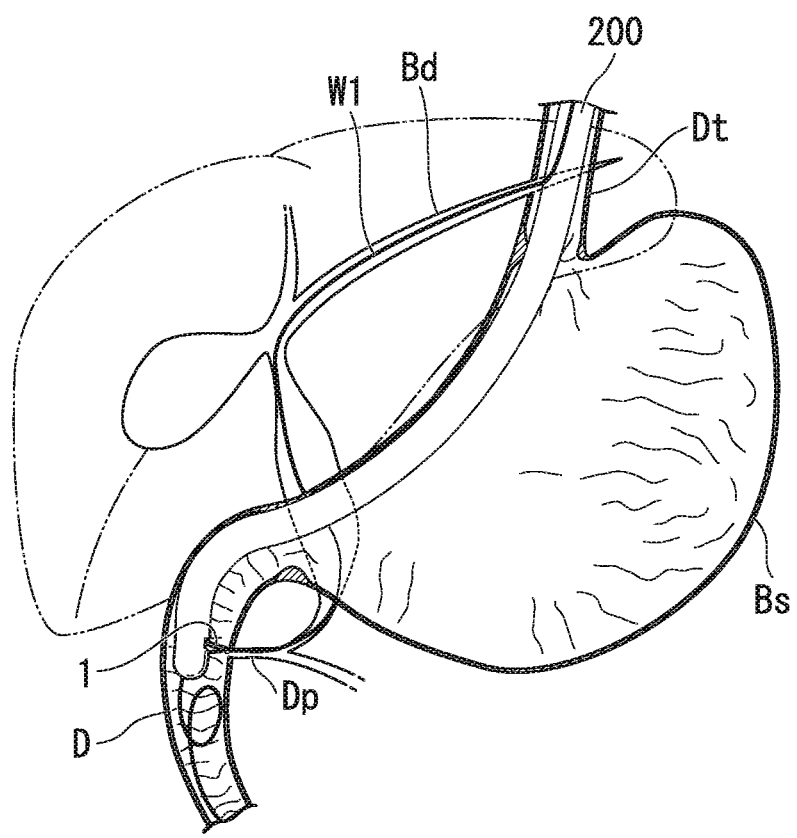
FIG. 9 is a diagram illustrating a method of introducing the medical instrument of the first embodiment of the present invention.
Figure 10:
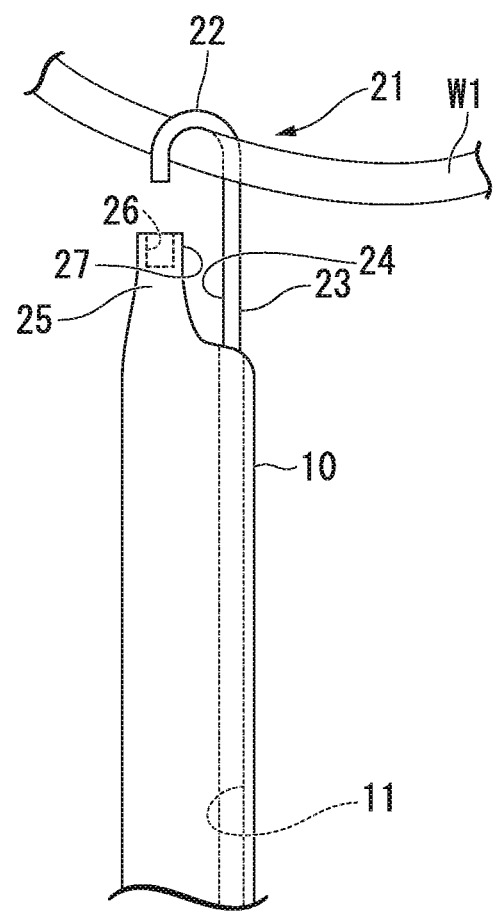
FIG. 10 is a diagram illustrating a method of introducing the medical instrument of the first embodiment of the present invention.
Figure 11:
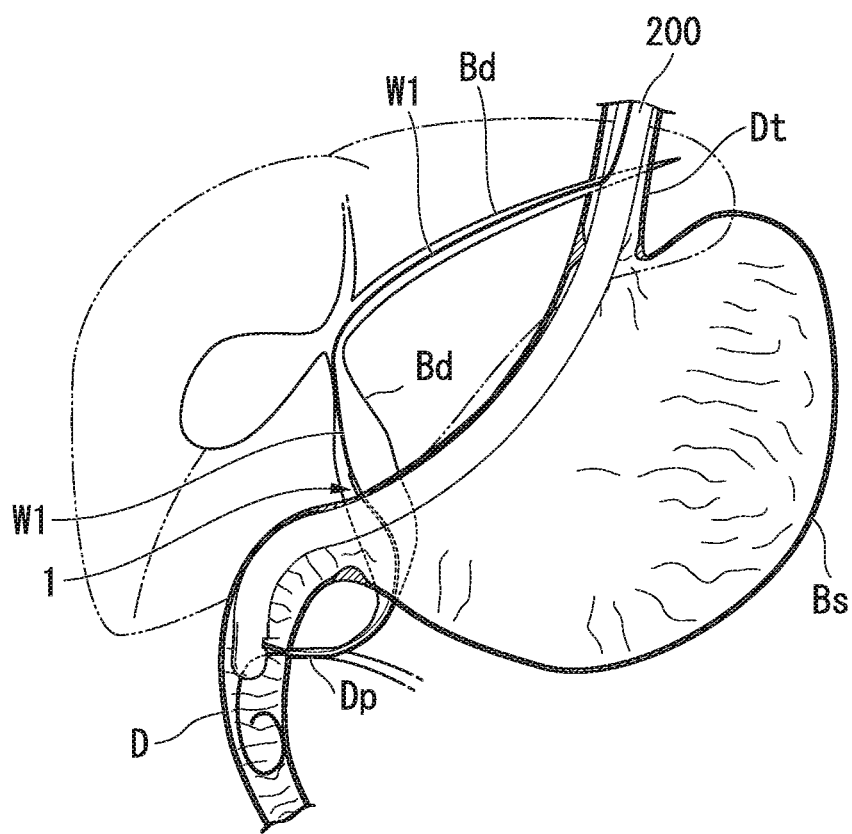
FIG. 11 is a diagram illustrating a method of introducing the medical instrument of the first embodiment of the present invention.
Figure 12:
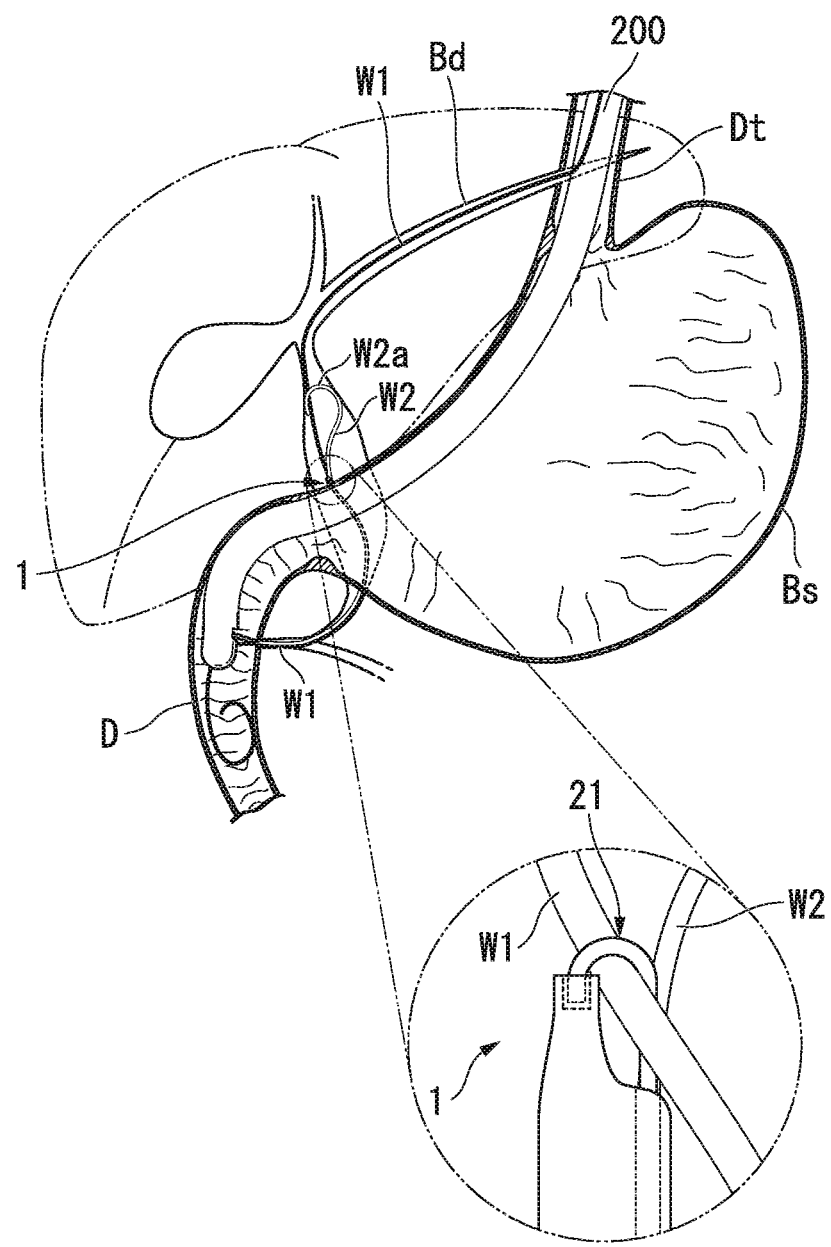
FIG. 12 is a diagram illustrating a method of introducing the medical instrument of the first embodiment of the present invention.

Next, as shown in FIG. 9, the hook member 21 is caused to protrude from the sheath 10 of the medical instrument 1 in a state where the first guide wire W1 protruding from the duodenal papilla Dp is confirmed with the image of the endoscope 200. Then, the hook portion 22 of the medical instrument 1 is hooked from the side substantially perpendicular to the first guide wire W1 as shown in FIG. 10. Then, as shown in FIG. 3, the hook member 21 is pulled into the lumen 11 of the sheath 10 and the distal end 22a of the hook portion 22 is inserted through the hole 26. At this time, the guide wire W1 is held at two points which are the contact point C1 and the contact point C2. When the guide wire W1 is pulled upward, the guide wire W1 rotates about the line connecting the contact point C1 and the contact point C2 and serving as the rotation axis, the guide wire W1 and the center axis O form an acute angle at the side at which the guide wire W1 is pulled, and the entire guide wire W1 and the medical instrument 1 also form generally an acute angle.

[Fifth Step]

Next, the surgeon pulls the proximal end side of the first guide wire W1 out of the patient's body toward the outside of the body. As a result of this operation, the medical instrument 1 is pulled into the bile duct Bd from the duodenal papilla Dp together with the first guide wire W1 in a state where the hook member 21 of the medical instrument 1 holds the medical instrument 1. Since an acute angle is formed between the guide wire W1 and the medical instrument 1, the guide wire W1 and the medical instrument 1 smoothly enter the bile duct Bd from the duodenal papilla Dp. In response to the pulling of the first guide wire W1, the distal end of the medical instrument 1 advances toward the upstream side at the inside of the bile duct Bd. Even at this time, as shown in FIG. 5, since an angle α formed between the guide wire W1 and the center axis O becomes an acute angle at the side at which the guide wire W1 is pulled, the sheath 10 is curved along the extension direction of the guide wire W. In this state, the medical instrument 1 advances inside the bile duct Bd.

[Sixth Step]

Next, the surgeon inserts the second guide wire W2 from a hand side into the sheath 10 inserted through the treatment instrument channel 201 of the endoscope 200 so that the second guide wire protrudes from the distal end of the sheath 10. Accordingly, as shown in 12, the second guide wire W2 is indwelled in the bile duct Bd from the distal end opening of the sheath 10. A distal end W2a of the second guide wire W2 also forms a loop like the first guide wire W1. At this time, the proximal end side of the second guide wire W2 is outside the patient's body.

[Seventh Step]

Figure 13:
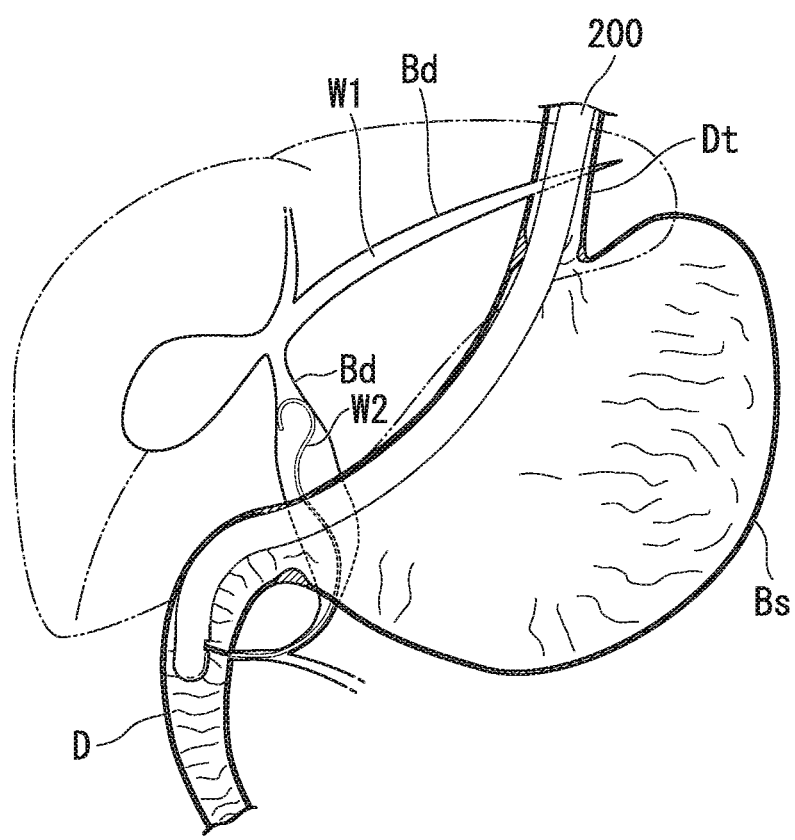
FIG. 13 is a diagram illustrating a method of introducing the medical instrument of the first embodiment of the present invention.

Next, the surgeon releases the holding of the first guide wire W1 by the medical instrument 1 and pulls the proximal end side of the first guide wire W1 toward the outside of the body so that the first guide wire is removed to the outside of the body. Further, as shown in FIG. 13, the surgeon retracts the medical instrument 1 so that the medical instrument is housed in the treatment instrument channel 201 of the endoscope 200 and the medical instrument 1 is removed to the outside of the body through the treatment instrument channel 201.

[Eighth Step]

Next, the same treatment as in ordinary ERCP (Endoscopic Retrograde Cholangiopancreatography) is performed using the second guide wire W2. Since the procedure of ERCP is the same as the known procedure, a description thereof will be omitted.

According to the medical instrument 1 of the present embodiment, when the guide wire W is positioned between the first protrusion portion 24 and the second protrusion portion 27, the guide wire W comes into point-contact with the first protrusion portion 24 and the second protrusion portion 27 and thus rotates about the line connecting the contact point C1 and the contact point C2 and serving as the rotation axis. Accordingly, the guide wire W can be held in a state where the longitudinal direction of the sheath 10 and the extension direction of the guide wire W1 are substantially parallel to each other. Thus, even when the rendezvous method is used, it is easy to introduce the medical instrument 1 from the duodenal papilla Dp by pulling the guide wire W. Therefore, it is possible to easily insert the medical instrument 1 from the duodenal papilla Dp toward the bile duct Bd even when the duodenal papilla Dp is stenosed or occluded. Further, it is possible to smoothly introduce the medical instrument even when the duodenal papilla Dp is not stenosed.

Further, it is possible to reliably hold the guide wire W without separating the guide wire W from the medical instrument 1 by advancing the distal end 22a of the hook portion 22 into the hole 26 of the protrusion portion 25.

Further, the hook member 21 and the protrusion portion 25 are arranged so that the protrusion direction of the first protrusion portion 24 and the protrusion direction of the second protrusion portion 27 face each other. Accordingly, since the rotation axis connecting the contact point C1 and the contact point C2 passes through the center axis of the guide wire W, it is possible to appropriately rotate the guide wire W by an operation of pulling the guide wire W held by the hook member 21 and the protrusion portion 25.

Further, a configuration has been described in which the hook portion 22 is formed in a substantially circular arc shape. However, the present invention is not limited thereto. That is, since the guide wire W may come into point-contact contact with the hook portion 22 at the contact points C1 and C2, the hook portion 22 may be formed in a shape in which a gap is formed between the inner peripheral surface 22b and the guide wire W.

Further, the hook member 21 and the protrusion portion 25 are arranged so that the protrusion direction of the first protrusion portion 24 faces the protrusion direction of the second protrusion portion 27. However, the present invention is not limited thereto.

Further, in the present embodiment, the hook member 21 and the protrusion portion 25 may be formed so that the first protrusion portion 24 faces the second protrusion portion 27. However, the guide wire W can rotate about the line connecting the contact point C1 and the contact point C2 and serving as the rotation axis even when the first protrusion portion 24 and the second protrusion portion 27 do not perfectly face each other as long as both portions face each other.

Figure 14:
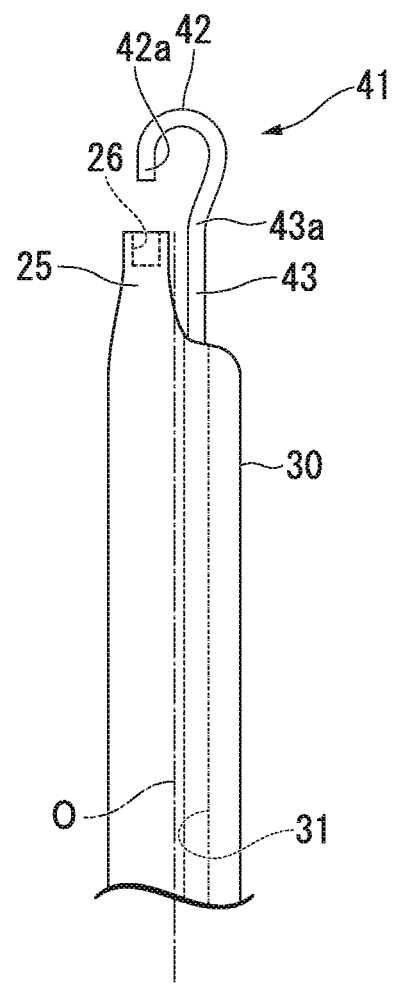
FIG. 14 is a diagram showing a modified example of a sheath of the medical instrument of the first embodiment of the present invention.
Figure 15:
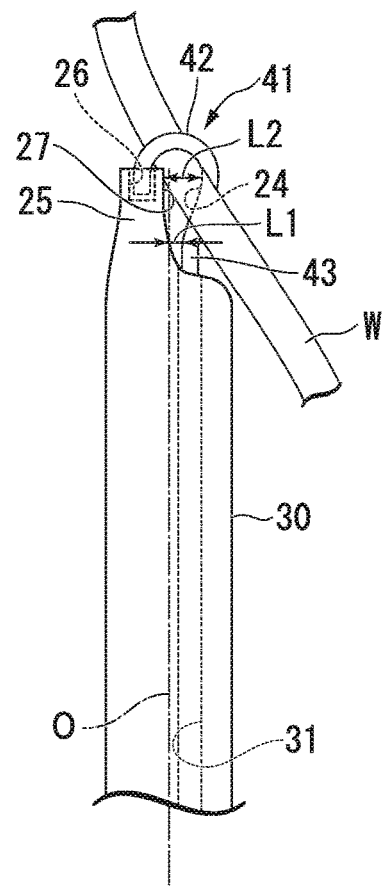
FIG. 15 is an overall view showing a state where the medical instrument of FIG. 14 holds a guide wire.
Figure 16:
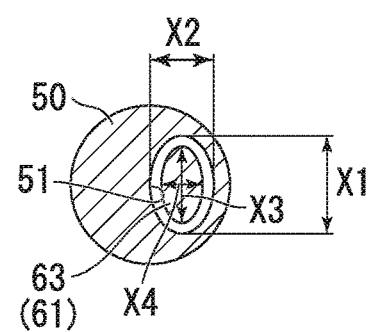
FIG. 16 is a cross-sectional view of a modified example when taken along a line XVI-XVI of the medical instrument of FIG. 1.

Further, a hook member 41 shown in a modified example of FIG. 14 may be used in the medical instrument of the present invention. The hook member 41 includes a hook portion 42 which is capable of holding the guide wire W and is formed at a distal end side and a columnar bar-shaped portion 43 which extends toward a proximal end side. The hook portion 42 and the bar-shaped portion 43 are integrally formed with each other. The hook portion 42 is swollen outward in the radial direction of a sheath 30 (in a direction moving away from a distal end 42a of the hook portion 42) from a distal end 43a of the bar-shaped portion 43 and is curved so that the distal end 42a of the hook portion 42 faces the proximal end side. Since the bar-shaped portion 43 of the present modified example is positioned near the distal end 42a of the hook portion 42 compared to the bar-shaped portion 23 of the first embodiment, a lumen 31 of the sheath 30 is positioned near the center axis O compared to the lumen 11 of the first embodiment. With such a configuration, as shown in FIG. 15, when the guide wire W is positioned between the first protrusion portion 24 and the second protrusion portion 27, a gap L2 between the first protrusion portion 24 and the second protrusion portion 27 at the distal end side of the hook member 41 (at the side of the hook portion 42) is larger than a gap L1 between the first protrusion portion 24 and the second protrusion portion 27 at the proximal end side of the hook member 41 (at the side of the bar-shaped portion 43).

In the present modified example, since the distal end 42a of the hook portion 42 and the distal end 43a of the bar-shaped portion 43 are close to each other, the gap L2 is larger than the gap L1. Accordingly, since the guide wire W is held at the distal end side of the hook member 41 rather than the proximal end side thereof, a rotation angle (rotation amount) at the time when the guide wire W is pulled can be large. Thus, since the angle α formed between the guide wire W and the center axis O is small, it is possible to hold the guide wire W in a state where the longitudinal direction of the sheath 30 and the extension direction of the guide wire W are substantially parallel to each other.

Further, since the guide wire W is automatically held at the further distal end of the holding portion, a step formed between the guide wire W and the holding portion is small and thus the guide wire more easily advances to the duodenal papilla Dp.

Further, the lumen 11 and the bar-shaped portion 23 are formed in a columnar shape. However, the present invention is not limited thereto. As shown in a modified example of FIG. 16, a cross-sectional shape of a lumen 51 of a sheath 50 in a direction perpendicular to the center axis O may include a long axis X1 and a short axis X2 and a cross-sectional shape of a bar-shaped portion 63 of a hook member 61 in a direction perpendicular to the center axis O (a cross-section taken along a line XVI-XVI of FIG. 1) may include a long axis X3 and a short axis X4. That is, the sheath 50 and the bar-shaped portion 63 may be flat. Further, a dimension of the long axis X3 of the bar-shaped portion 63 is larger than a dimension of the short axis X2 of the lumen 51. Accordingly, since a position of the bar-shaped portion 63 in the rotation direction of the lumen 51 of the sheath 50 is determined, the distal end 22a of the hook portion 22 easily enters the hole 26.

Further, the sheath 10 may have pre-curvature (permanent bending) so as to follow the guide wire W. In such a configuration, since the sheath 10 follows the guide wire W, the sheath is easily inserted into the duodenal papilla Dp. Furthermore, when the hook member 21 has the same permanent bending as the permanent bending of the sheath 10, the sheath 10 is easily bent.

Further, since the pre-curvature (permanent bending) of the sheath 10 follows a bent portion of a forceps support of the distal end of the endoscope, the hook member 61 can be normally arranged in the same direction as that of the endoscope.

Further, a metal plate may be provided in the hole 26. Accordingly, since the hole 26 is reinforced, the distal end 22a of the hook portion 22 can be reliably held after the distal end 22a of the hook portion 22 is advanced into the hole 26.

[Second Embodiment]

A second embodiment of the present invention will be described with reference to FIGS. 17 to 22.

A medical instrument 70 of the present embodiment is different from that of the first embodiment in that a sheath and a holding portion have different configurations.

In the description below, the same reference numerals will be given to the same components as those of the description above and a repetitive description thereof will not be made.

Figure 17:
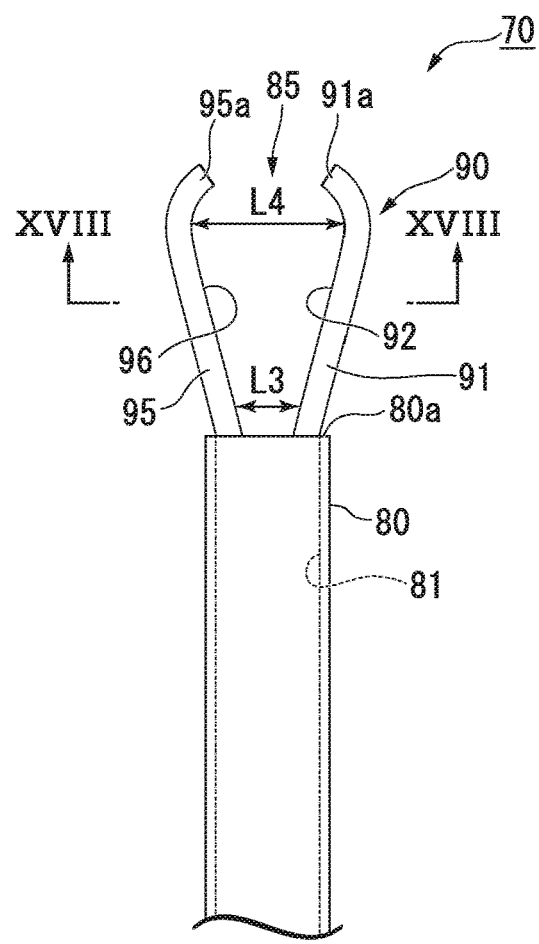
FIG. 17 is an overall view showing a medical instrument of a second embodiment of the present invention.

In the present embodiment, the protrusion portion protruding forward from the distal end of the sheath as in the first embodiment is not provided. A sheath 80 has, as shown in FIG. 17, a substantially tube shape and is formed in a tube shape having a center axis O.

A grasping portion (holding portion) 90 has a configuration in which a first grasping portion 91 and a second grasping portion 95 are arranged to be capable of advancing and retracting in a lumen 81 of the sheath 80. The grasping portion 90 of the present embodiment is a two-legged forceps in which the first grasping portion 91 and the second grasping portion 95 are opened and closed while being capable of advancing and retracting relative to the sheath 80. A distal end of the first grasping portion 91 is provided with a convex portion 91a which protrudes inward in the radial direction of the sheath 80. A distal end of the second grasping portion 95 is also provided with a convex portion 95a which protrudes inward in the radial direction of the sheath 80. An opening 85 into which the guide wire W is insertable is provided between the convex portion 91a and the convex portion 95a.

A gap L4 between the first grasping portion 91 and the second grasping portion 95 at a distal end side of the grasping portion 90 protruding from the sheath 10 is larger than a gap L3 between the first grasping portion 91 and the second grasping portion 95 at a proximal end side thereof. That is, a gap between the first grasping portion 91 and the second grasping portion 95 gradually becomes larger from the proximal end side toward the distal end side.

Figure 18:
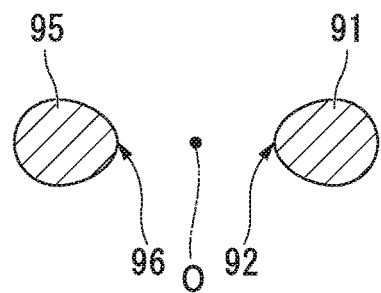
FIG. 18 is a cross-sectional view taken along a line XVIII-XVIII of FIG. 17.

As shown in FIG. 18 in a cross-section perpendicular to the longitudinal direction of the first grasping portion 91, the first grasping portion 91 includes a first protrusion portion 92 which protrudes inward in the radial direction of the sheath 80. Similarly, the second grasping portion 95 includes a second protrusion portion 96 which protrudes inward in the radial direction of the sheath 80. The first protrusion portion 92 and the second protrusion portion 96 are provided to have a uniform range in the extension direction. The first protrusion portion 92 and the second protrusion portion 96 may be provided at least at a portion which protrudes from a distal end 80a of the sheath 80 in the first protrusion portion 92 and the second protrusion portion 96.

Further, the first grasping portion 91 and the second grasping portion 95 are arranged with a gap formed therebetween so that the first protrusion portion 92 and the second protrusion portion 96 face each other with the center axis O therebetween.

Figure 19:
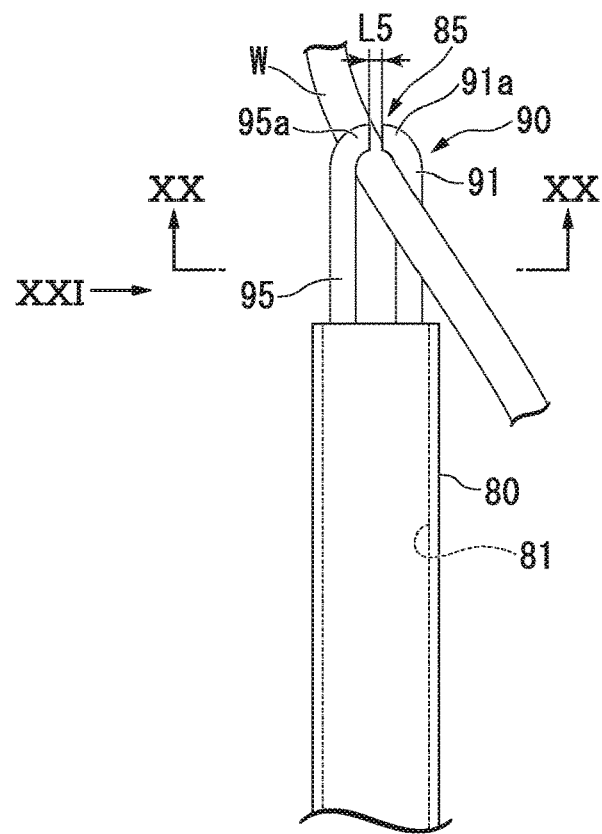
FIG. 19 is an overall view showing a state where the medical instrument of FIG. 17 holds a guide wire.

As shown in FIG. 19, when the guide wire W is positioned between the first protrusion portion 92 and the second protrusion portion 96 and the hook member 21 is retracted, the first grasping portion 91 and the second grasping portion 95 are closed. At this time, since the convex portion 91a and the convex portion 95a move close to each other, a distance L5 of the opening 85 in the radial direction becomes smaller than an outer diameter D1 (see FIG. 20) of the guide wire W. Accordingly, it is possible to prevent the guide wire W from being separated from the opening 85.

Further, the first grasping portion 91 and the second grasping portion 95 are arranged in parallel when the guide wire W is grasped. That is, the first grasping portion 91 and the second grasping portion 95 are arranged so that the protrusion direction of the first protrusion portion 92 and the protrusion direction of the second protrusion portion 96 face each other.

Figure 20:
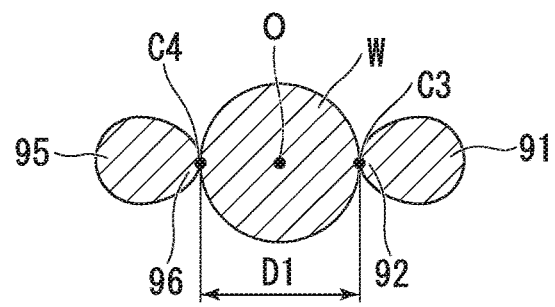
FIG. 20 is a cross-sectional view taken along a line XX-XX of FIG. 19.
Figure 21:
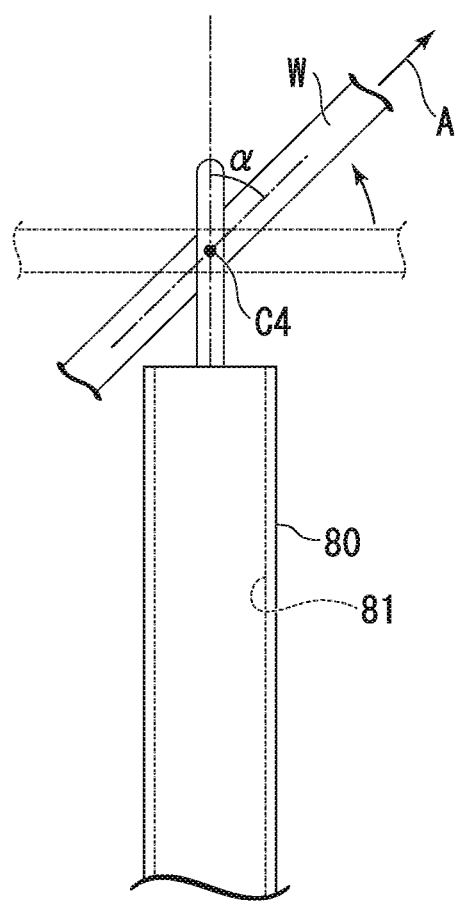
FIG. 21 is a diagram when viewed from a direction XXI of FIG. 19.

Further, as shown in FIG. 20, the guide wire W comes into point-contact with the first protrusion portion 92 at a contact point C3 and the guide wire W comes into point-contact with the second protrusion portion 96 at a contact point C4. At this time, the guide wire W comes into point-contact with the grasping portion 90. For this reason, when the guide wire W is pulled upward (in a direction indicated by an arrow A) as shown in FIG. 21, the guide wire W rotates about a line connecting the contact point C3 and the contact point C4 and serving as a rotation axis and the guide wire W and the center axis O form an acute angle at the side at which the guide wire W is pulled. That is, an angle α formed between the guide wire W and the center axis O becomes an acute angle.

When a medical instrument 40 is introduced into a bile duct, a method which is different from the method shown in the first embodiment only in the fourth step is performed.

In the present embodiment, in the fourth step, the guide wire W is clamped by the first grasping portion 91 and the second grasping portion 95 of the medical instrument 40 in a state where the guide wire W protruding from the duodenal papilla Dp is confirmed with an endoscopic image. At this time, when the grasping portion 90 is pulled toward the lumen 81 even if the guide wire W is grasped at the proximal end side of the grasping portion 90 protruding from the distal end 80a of the sheath 80, the guide wire W moves toward the distal end side. Then, as shown in FIG. 19, the first grasping portion 91 and the second grasping portion 95 are closed in a state where the guide wire W is grasped at the distal end side. The guide wire W is grasped at two points which are the contact point C3 and the contact point C4. When the guide wire W is pulled upward, the guide wire W rotates about the line connecting the contact points C3 and C4 and serving as the rotation axis, the guide wire W and the center axis O form an acute angle at the side at which the guide wire W is pulled, and the entire guide wire W and the medical instrument 1 also form generally an acute angle.

According to the medical instrument 70 of the present embodiment, since the grasping portion 90 includes the opening 85 at the distal end thereof, the guide wire W is arranged between the first grasping portion 91 and the second grasping portion 95 in such a manner that the opening 85 protrudes toward the guide wire W. That is, the guide wire W can be inserted into the opening 85 by a small movement amount. Furthermore, the guide wire W can be appropriately inserted into the opening 85 even in a narrow space.

Further, since the grasping portion 90 is closed in such a manner that the grasping portion 90 is pulled toward the lumen 81 of the sheath 80, the guide wire W can be grasped by a simple operation. Accordingly, it is possible to hold the guide wire W in a state where the longitudinal direction of the sheath 80 and the extension direction of the guide wire W are substantially parallel to each other.

Further, since the first grasping portion 91 and the second grasping portion 95 are arranged so that the protrusion direction of the first protrusion portion 92 and the protrusion direction of the second protrusion portion 96 face each other and the rotation axis connecting the contact point C3 and the contact point C4 passes through the center axis of the guide wire W, it is possible to appropriately rotate the guide wire W by an operation of pulling the guide wire W held by the grasping portion 90.

Figure 22:
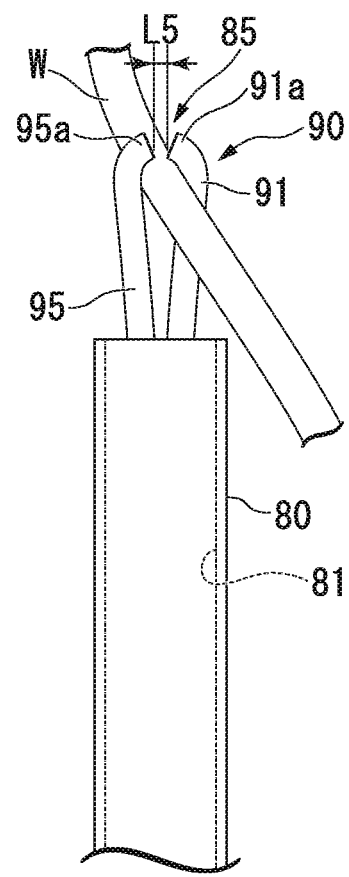
FIG. 22 is a diagram showing a modified example of the medical instrument of the second embodiment of the present invention.

Further, in the above-described example, the first grasping portion 91 and the second grasping portion 95 are arranged in parallel when the guide wire W is grasped. However, as shown in FIG. 22, the first grasping portion 91 and the second grasping portion 95 may grasp the guide wire W in a state where the first grasping portion 91 and the second grasping portion 95 forms an angle therebetween. Accordingly, since the guide wire W is automatically held at the further distal end of the grasping portion 90, a step formed between the guide wire W and the grasping portion 90 is small and thus the guide wire more easily advances to the duodenal papilla Dp.

While the preferred embodiments of the present invention have been described above, the present invention is not limited to these embodiments. Additions, omissions, substitutions, and other modifications of the configurations can be made without departing from the spirit of the present invention.

Figure 23:
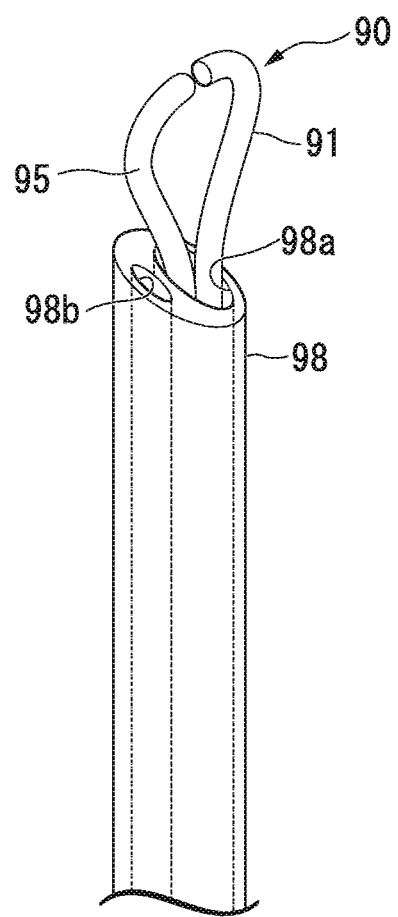
FIG. 23 is a diagram showing a modified example of a sheath of the medical instrument of the present invention.

For example, a configuration using a sheath 98 including a first lumen 98a and a second lumen 98b as in a modified example of FIG. 23 may be used in the medical instrument of the present invention. The first lumen 98a and the second lumen 98b are arranged in parallel in the longitudinal direction. With such a configuration, for example, the two-legged forceps (holding portion) 90 can be inserted through the first lumen 98a and a visualizing agent can flow to the second lumen 98b. Thus, it is possible to check the state of the bile duct by the flowing of a visualizing agent when the medical instrument is introduced into a bile duct. Further, the guide wire W2 may be inserted into the second lumen 98b. Since the hook member 21 and the guide wire W2 are arranged in different lumens, interference therebetween does not occur.

Further, even in the first embodiment, since the hole 26 is formed to the proximal end of the sheath 10, the second lumen can be provided.

[Additional Note]

The present invention includes the following technical idea.

Provided is a method of inserting a medical instrument, including a sheath having a center axis and having a first contact area capable of contacting the guide wire and a second contact area capable of contacting the guide wire and provided at a proximal end side in relation to the first contact area and a holding portion arranged to be capable of advancing and retracting in a lumen of the sheath and holding the guide wire, into a hollow organ, the method including steps of: inserting a distal end of the guide wire into a first hollow organ from the outside of a body; causing the guide wire inserted into the first hollow organ to protrude from an opening of the first hollow organ into a second hollow organ communicating with the first hollow organ through the opening of the first hollow organ so that a distal end part of the guide wire indwells therein; inserting an endoscope to the second hollow organ and inserting the medical instrument through a treatment instrument channel of the endoscope so that the medical instrument protrudes from the endoscope; holding the guide wire by the holding portion of the medical instrument so that the guide wire contacts the first contact area and the second contact area; and pulling the guide wire from the outside of the body so that a distal end of the medical instrument is pulled from the second hollow organ into the first hollow organ through the opening.

While the preferred embodiments of the present invention have been described above, the present invention is not limited to these embodiments and modified examples thereof. It is should be understood that additions, omissions, substitutions, and other modifications of the configurations can be made without departing from the spirit of the present invention.

Also, the present invention is not limited by the description above and is limited only by the scope of the appended claims.

The invention claimed is:

1. A medical instrument which grips a wire, comprising:
   a sheath which has a longitudinal axis;
   a first holder which protrudes from a distal end of the sheath, the first holder including a first protrusion protruding inward in a radial direction of the sheath, the first protrusion having two surfaces terminating in a first edge, the first edge extending in a direction parallel to the longitudinal axis so as to face the center axis of the sheath when viewed along a cross-section perpendicular to the longitudinal axis; and
   a second holder which protrudes from the distal end of the sheath, the second holder including a second protrusion, the second protrusion being provided in the distal end of the sheath, the second protrusion protruding toward a center axis of the sheath, a protrusion direction of the second protrusion facing a protrusion direction of the first protrusion, the second protrusion having two surfaces terminating in a second edge, the second edge extending in a direction parallel to the longitudinal axis so as to face the center axis of the sheath when viewed along the cross-section perpendicular to the longitudinal axis,
   wherein the first holder and the second holder are arranged with a gap therebetween so that a space in which a wire is held between the first edge and the second edge is formed, and
   wherein the first holder or the second holder is capable of moving so that a distance between a distal end of the first holder and a distal end of the second holder changes from a first dimension which is larger than a diameter of the wire to a second dimension which is smaller than the diameter of the wire, and the space is formed by the first holder and the second holder such that the wire is capable of rotating about a line connecting a first contact point where the first edge contacts with the wire with a second contact point where the second edge contacts with the wire and the wire is capable of rotating in a state where the wire is contacted and held so as to be sandwiched by the first edge and the second edge.

2. The medical instrument according to claim 1, wherein the first holder and the second holder are arranged so that a protrusion direction of the first protrusion and a protrusion direction of the second protrusion directly face each other.

3. The medical instrument according to claim 1, wherein the gap between the first edge and the second edge is larger at the distal end side of the first holder and the second holder than at the proximal end side of the first holder and the second holder.

4. The medical instrument according to claim 1, wherein the first protrusion is arranged at a distal end portion of the first holder and the second protrusion is arranged at a distal end portion of the second holder.

5. The medical instrument according to claim 1,
wherein the first holder is a hook member that is capable of holding the wire by hooking the wire,
wherein the second holder is a protrusion which protrudes outward from the distal end of the sheath,
wherein the protrusion is provided with a hole which is parallel to the longitudinal axis, and
wherein a distal end of the hook member is capable of entering the hole.

6. The medical instrument according to claim 5,
wherein a cross-sectional shape of a lumen of the sheath perpendicular to the longitudinal axis includes a long axis and a short axis, and
wherein a cross-sectional shape of the hook member includes a long axis and a short axis.

7. The medical instrument according to claim 1,
wherein an opening into which the wire is insertable is formed by the distal end of the first holder and the distal end of the second holder, and
wherein a dimension of the opening in the radial direction when the wire comes into point-contact with the first holder and the second holder is smaller than the diameter of the wire.

8. The medical instrument according to claim 1, wherein a lumen which is arranged along a lumen of the sheath and is different from the lumen is further provided.

9. A medical system comprising:
the wire; and
the medical instrument according to claim 1.

* * * * *